United States Patent [19]

Haugwitz et al.

[11] 4,127,664
[45] Nov. 28, 1978

[54] METHOD FOR TREATING BLACKHEAD DISEASE

[75] Inventors: Rudiger D. Haugwitz, Titusville; Larry R. Cruthers, Flemington, both of N.J.

[73] Assignee: E. R. Squibb & Sons, Inc., Princeton, N.J.

[21] Appl. No.: 850,583

[22] Filed: Nov. 11, 1977

[51] Int. Cl.$^2$ .................................................. A61K 31/415
[52] U.S. Cl. .................................................. 424/273 R
[58] Field of Search .................................................. 424/273

[56] References Cited

U.S. PATENT DOCUMENTS

| | | | |
|---|---|---|---|
| 3,929,824 | 12/1975 | Beard et al. | 548/306 |
| 4,000,300 | 12/1976 | Mitrovic | 424/273 |

Primary Examiner—Sam Rosen
Attorney, Agent, or Firm—Lawrence S. Levinson; Merle J. Smith; Burton Rodney

[57] ABSTRACT

A method is provided for treating or preventing blackhead disease in birds by administering to birds, especially to poultry, such as turkeys, benzimidazoles having the structure

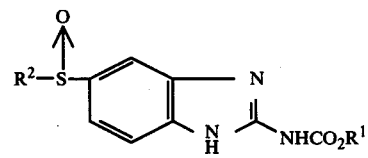

wherein $R^1$ is lower alkyl or phenyl-lower alkyl, and $R^2$ is lower alkyl, cycloalkyl, cycloalkylalkyl, cycloalkenyl, cycloalkenylalkyl, phenyl, benzyl and phenylethyl dispersed in a non-toxic physiologically acceptable carrier.

15 Claims, No Drawings

METHOD FOR TREATING BLACKHEAD DISEASE

BACKGROUND OF THE INVENTION

U.S. Pat. No. 4,000,300 to Mitrovic, assigned to Hoffmann-LaRoche, discloses the use of 2-carbalkoxy-aminobenzimidazole 5(6)-phenyl ethers represented by the formula

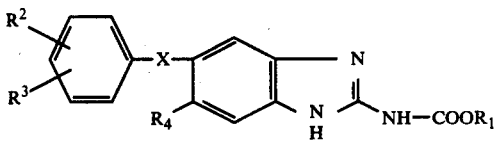

wherein $R_1$ is alkyl having from 1 to 4 carbon atoms, $R_2$ and $R_3$, which may be the same or different, each are hydrogen, hydroxy, alkoxy having from 1 to 4 carbon atoms, halogen, trifluoromethyl, alkyl having from 1 to 4 carbon atoms or carbalkoxy having from 1 to 4 carbon atoms in the alkoxy group, $R_4$ is hydrogen or chlorine and X is oxygen or sulfur, for preventing and curing blackhead disease in birds, such as turkeys.

U.S. Pat. No. 4,046,908 to Haugwitz, assigned to Squibb, discloses benzimidazole derivatives of the structure

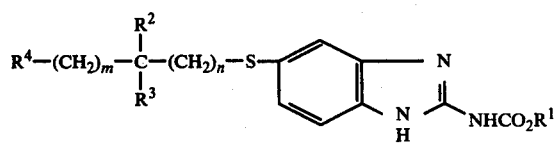

wherein $R^1$ is lower alkyl, phenyl-lower alkyl, halo-lower alkyl, mono-lower alkylaminoalkyl, di-lower alkylaminoalkyl, and alkyl pyridinium halide, $R^2$ and $R^3$ may be the same or different and are hydrogen or lower alkyl, $R^4$ is cycloalkyl or cycloalkenyl, and m is 0 to 3, n is 0 to 3, and $m + n \leq 5$ and U.S. Pat. No. 4,025,638 to Gyurik, assigned to Smith Kline, discloses 5-cycloalkylthio- or oxy-2-carbalkoxyaminobenzimidazoles for their use as anthelmintic agents.

In addition, other benzimidazole compounds are known for their use as anthelmintic agents. For example, U.S. Pat. No. 3,574,845 to Actor et al., assigned to Smith Kline, discloses 5(6)-benzene ring substituted benzimidazole-2-carbamate derivatives including 5(6)-methylthio-2-carboethoxyaminobenzimidazole and various 5(6)-alkyl-2-carbomethoxyaminobenzimidazoles;

U.S. Pat. Nos. 3,929,821 and 4,002,640 to Beard et al. and assigned to Syntex disclose various 5(6)-benzene ring substituted benzimidazole-2-carbamate derivatives including 5(6)-alkylsulfinyl-2-carbomethoxyaminobenzimidazoles, as well as 5(6)-benzylsulfinyl-2-carbomethoxyaminobenzimidazole, 5(6)-phenylsulfinyl-2-carbomethoxyaminobenzimidazole, 5(6)-cycloalkylsulfinyl-2-carbomethoxyaminobenzimidazoles and 5(6)-cyclopropylmethylsulfinyl-2-carbomethoxyaminobenzimidazole; and U.S. Pat. Nos. 3,954,791 to Loewe et al. and 3,928,375 to Duwel et al., disclose 2-carbalkoxy-aminobenzimidazole-5(6)-phenyl and phenylthio ethers.

Other benzimidazoles useful as anthelmintic agents are disclosed in U.S. Pat. Nos. 3,929,822, 3,929,823, 3,929,824, 3,935,209, 3,965,113 and 4,005,202 all to Beard et al. and assigned to Syntex; U.S. Pat. Nos. 3,682,952 to Actor et al., 3,578,676 and 3,694,455 to Dunn, 3,915,986 and 3,969,526 to Gyurik, all assigned to Smith Kline; and U.S. Pat. No. 3,738,993 to Haugwitz et al., assigned to Squibb.

DESCRIPTION OF THE INVENTION

The present invention relates to a method for treating or preventing blackhead disease in birds, especially poultry such as turkeys, by administering to a bird a sulfoxide derivative of a benzimidazole having the structure

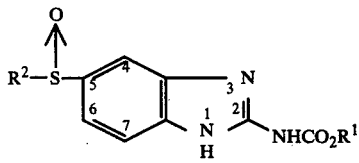

wherein $R^1$ is lower alkyl or phenyl-lower alkyl, and $R^2$ is cycloalkyl, cycloalkylalkyl, cycloalkenyl, cycloalkenylalkyl, lower alkyl, benzyl, phenylethyl or phenyl.

The term "lower alkyl" or "alkyl" as used herein includes straight or branched chain aliphatic hydrocarbon radicals having up to and including seven carbon atoms, such as methyl, ethyl, propyl, isopropyl, n-butyl, isobutyl, t-butyl, amyl, hexyl, heptyl and the like.

The term "lower alkoxy" or alkoxy" refers to a lower alkyl group as defined above attached to an oxygen.

The term "phenyl" includes unsubstituted phenyl as well as substituted phenyl including one or two substituents such as hydroxyl, lower alkyl, lower alkoxy, halogen, trifluoromethyl, carbalkoxy, nitro or amino, with the substituents preferably being in the ortho and/or para positions.

The term "halogen" or "halo" as employed herein refers to chlorine, bromine, iodine or fluorine with chlorine and bromine being preferred.

The term "phenyl lower alkyl" as used herein refers to lower alkyl groups as discussed above having a phenyl substituent, such as benzyl.

The term "cycloalkyl" includes cyclic hydrocarbon groups containing 3 to 12 carbons optionally substituted with 1, 2 or 3 halogen groups and/or 1, 2 or 3 alkyl groups. The term "cycloalkenyl" includes cyclic hydrocarbon groups containing 3 to 10 carbons and a single C—C double bond provided that the double bond is not on the alpha carbon atom, which may optionally be substituted with 1, 2 or 3 halogen groups and/or 1, 2 or 3 alkyl groups. Examples of suitable cycloalkyl and cycloalkenyl groups include cyclopropyl, cyclobutyl, cyclopentyl, 2,2-dichloro-cyclopropyl, 2-methyl-cyclobutyl, 2,2-dichloro-1-methyl-cyclopropyl, 2-methyl-cyclopropyl, 2,4-dimethylcyclohexyl, 2-bromocycloheptyl, 3,4-dichloro-cyclooctyl, 2,4,6-triethylcyclodecyl and 3-chloro-cyclododecyl, cyclopropenyl, cyclobutenyl, cyclohexenyl, cycloheptenyl, cyclononenyl and cyclodecenyl, any of which cycloalkenyl groups may be substituted with 1, 2 or 3 halogen and/or lower alkyl groups.

The terms "cycloalkylalkyl" and "cycloakenylalkyl" refer to cycloalkyl and cycloalkenyl groups as defined above attached to a lower alkyl group as defined above.

Preferred compounds for use in the method of the invention are those wherein $R^1$ is methyl, ethyl, propyl or benzyl, $R^2$ is cycloalkylalkyl, or alkyl. Most preferred are compounds wherein $R^2$ is cycloalkylalkyl, such as cyclopropylmethyl and cyclobutylmethyl.

Examples of compounds which may be employed in the method of the present invention include the following.

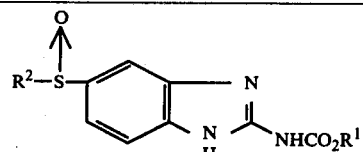

|     | $R^1$      | $R^2$       |
|-----|------------|-------------|
| 1.  | $CH_3$     | $CH_3$      |
| 2.  | $CH_3$     | $C_2H_5$    |
| 3.  | $C_2H_5$   | $n-C_3H_7$  |
| 4.  | $C_3H_7$   | $n-C_4H_9$  |
| 5.  | $CH_3$     | $n-C_5H_{11}$ |
| 6.  | $C_6H_5CH_2$ | $C_2H_5$  |
| 7.  | $C_6H_5CH_2$ | $CH_3$    |
| 8.  | $CH_3$     | $i-C_3H_7$  |
| 9.  | $CH_3$     | $i-C_4H_9$  |
| 10. | $C_2H_5$   | $n-C_6H_{13}$ |
| 11. | $CH_3$     | $t-C_4H_9$  |
| 12. | $CH_3$     | 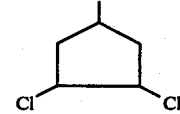 |
| 13. | $CH_3$     |  |
| 14. | $C_6H_5CH_2$ |  |
| 15. | $C_2H_5$   |  |
| 16. | $C_2H_5$   | 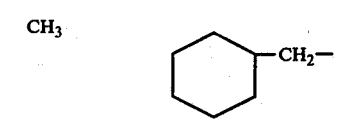 |
| 17. | $C_6H_5CH_2$ |  |
| 18. | $CH_3$     |  |
| 19. | $C_3H_7$   | 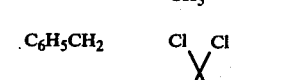 |

-continued

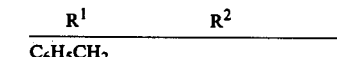

|     | $R^1$        | $R^2$                |
|-----|--------------|----------------------|
| 20. | $C_6H_5CH_2$ |  |
| 21. | $CH_3$       |  |
| 22. | $CH_3$       |  |
| 23. | $CH_3$       |  |
| 24. | $CH_3$       | 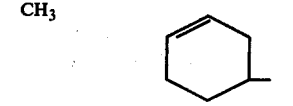 |
| 25. | $CH_3$       |  |
| 26. | $C_2H_5$     |  |
| 27. | $C_6H_5CH_2$ |  |
| 28. | $C_2H_5$     |  |
| 29. | $CH_3$       |  |
| 30. | $C_2H_5$     |  |
| 31. | $CH_3$       |  |
| 32. | $CH_3$       |  |

-continued

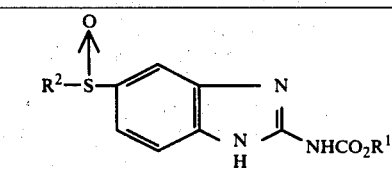

| | R¹ | R² |
|---|---|---|
| 33. | C₃H₇ | 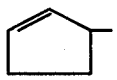 |
| 34. | CH₃ |  |
| 35. | C₂H₅ |  |
| 36. | CH₃ | 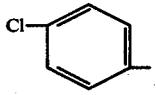 |
| 37. | CH₃ | 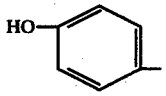 |
| 38. | CH₃ | 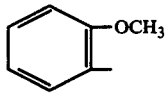 |
| 39. | C₂H₅ | 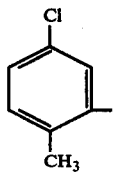 |
| 40. | CH₃ | 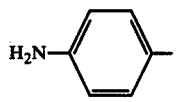 |
| 41. | C₂H₅ |  |
| 42. | C₃H₇ | 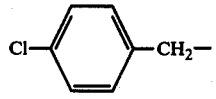 |
| 43. | CH₃ | 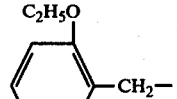 |
| 44. | CH₃ | 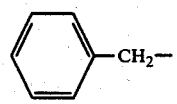 |

-continued

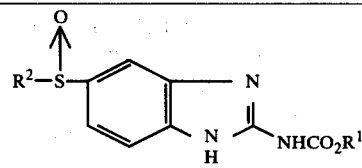

| | R¹ | R² |
|---|---|---|
| 45. | CH₃ | 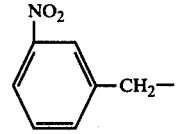 |
| 46. | CH₃ | 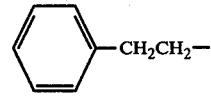 |
| 47. | C₆H₅CH₂ | 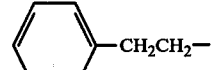 |

The benzimidazole derivatives of structure I may be prepared as described in U.S. Pat. Nos. 3,929,821 and 4,002,640 to Beard et al. and in copending applications Ser. Nos. 769,632, filed Feb. 17, 1977 and 769,634, filed Feb. 17, 1977, which are incorporated herein by reference.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anti-histomonal activity and are useful in the treatment and/or prevention of infectious enterohepatitis, commonly referred to as histomoniasis or blackhead disease.

Blackhead disease, which is caused by the protozoan *Histomanas meleagridis*, occurs in birds. Its economic impact in terms of losses is greatest in turkeys. However, other poultry and birds, e.g., chickens, guineas, quails, pheasants and pea-fowl, also contract the disease. Its clinical symptoms are manifested by lesions and inflammation of the ceca and liver.

*Histomonas meleagridis* is mostly harbored by the common poultry cecal worms, *Heterakis gallinarum*, and its eggs, in which it is able to live for extended periods. The disease is contracted orally by the birds when consuming feed or water contaminated with droppings containing the infectious organism or by swallowing cecal worms or their eggs harboring the parasite. The incubation period of blackhead is about 14 to 21 days. The disease manifests itself in the infected birds by inappetence, a constant yellowish or sulfur colored diarrhea and weight loss followed by death. Generally, young birds are more susceptible than adults, although the mortality rate in both groups is very high. Adult birds are usually sick for several days losing much weight before they die while the young birds succumb much quicker.

Post-mortem examinations of the birds disclose multiple lesions and ulcerations of the cecal wall and liver. The ceca are filled with yellowish-green cores and the cecal walls are thickened. The lesions of the liver consist of large irregular reddened or gray necrotic areas. In treating birds, the compounds are given orally; however, other routes such as parenterally, for example, subcutaneously, intravenously, interperitoneally and intramuscularly may be employed.

The compounds are administered orally in admixture with drinking water or feed. They may be mixed with a nontoxic, edible carrier to form a feed supplement, or be administered in unit dosage forms such as powders, capsule, tablet, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and benzyl benzoate: sesame oil: benzyl benzoate (1:1). The parenteral product will usually take the form of a suspension containing from about 0.001 to about 10% by weight of the compound of formula I in anyone or mixture of the above carriers.

In general, the compounds of formula I exhibit antihistomonal activity when administered to birds (parenterally or orally) in a single dose of about 0.5 to about 100 mg per kilogram of animal body weight. It is preferred to employ in the range of 1–25 mg per kilogram of body weight. The compounds may be divided into a plurality of smaller doses given parenterally or orally over one or more days.

When the compounds of formula I are to be administered in unit dosage form, capsules, boluses or drenches containing the desired amount of active compound distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of formula I are present as an active ingredient. A typical feed supplement comprises the anti-histomonal agent intimately dispersed in or admixed with an inert carrier or diluent, i.e., one that is nonreactive with respect to the anti-histomonal agent and that may be administered with safety to the animals. The carrier or diluent is preferably one that is or may be an ingredient of an animal ration. This composition may be mixed with the feed to give any useful desired concentration, preferably about 0.002–2%. Lastly feeds containing the active ingredient may be made directly by mixing said active ingredient in a feed which is inert to said anti-histomonal compounds so as to give feeds having concentrations of anti-histomonal agent of from 0.1–2%.

More specifically, the compositions will contain from about 0.003 to 0.05% by weight of the active compounds. Generally from 0.003 gram to 0.05 gram per hundred grams of feed or water or other inert carrier of the active compound is used in treating the birds. Generally, when the inert carrier is dry feed, from 0.006 gram to 0.1 gram of active compound per hundred grams of feed is used and when the inert carrier is water, from 0.003 gram to 0.05 gram of active compound per 100 cc. of water is used. This treatment results in substantially complete prevention and control of the disease. The particular dosage depends upon the specific composition used and the method of administration. The preferred method of treatment is by oral administration, e.g., in the feed, in the drinking water, or in other ingestable inert carriers. Generally, a bird will take in, on a weight basis, about twice as much water as dry feed. Thus, the dosage of histomonostat in water is about half that in the feed. The preferred preventive dosage in feed is about 0.01 gram per 100 grams of feed. In drinking water the preferred preventive dosage is about 0.003 gram per 100 cc. of water. For therapy, usually twice the preventive dosage is used. The amount of active compound which an individual bird ingests depends on the amount of feed or water ingested. This varies with the individual bird. Usually, about 3 mg/kg for older birds and about 6 mg/kg for younger birds of active compound per day are ingested when the firds are allowed free access to the feed and half these amounts when allowed free access to drinking water.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

Feed Composition Containing [5-[(Cyclopropylmethyl)sulfinyl]-1H-benzimidazol-2-yl]carbamic acid, methyl ester A. 4-(Cyclopropylmethyl)thio-2-nitroaniline To a stirred mixture of 11.7 g (0.06 mole) of 2-nitro-4-thiocyanoaniline in 500 ml of absolute ethanol under nitrogen there is added 2.5 g (0.06 mole) of sodium borohydride in portions. The mixture is stirred at room temperature for 15 minutes and then refluxed for 15 minutes. The heating mantle is removed and 3.9 g (0.06 mole) of KOH in 25 ml of absolute ethanol is added. The mixture is stirred for 1 minute. A solution of 4.8 g (0.06 mole) of (chloromethyl)cyclopropane in 10 ml of absolute ethanol is added and the mixture is stirred at room temperature for 15 minutes then refluxed for 2 hours. Equal amounts of water and $CHCl_3$ are added until 2 layers are formed. The organic layer is separated, dried ($MgSO_4$), and the solvent removed in vacuo to give 9.1 g of an orange-red solid, m.p. 45°–47°.

B. 4-(Cyclopropylmethyl)thio-o-phenylenediamine

A mixture of 6.75 g (0.03 mole) of 4-(cyclopropylmethyl)thio-2-nitroaniline and 0.5 g of $PtO_2$ in 200 ml of absolute ethanol is reduced on the Parr hydrogenator at 50 psi. The mixture is filtered and the solvent is removed in vacuo to yield the solid diamine, m.p. 57°–60° C.

C. [5-[(Cyclopropylmethyl)thio]-1H-benzimidazol-2-yl]carbamic acid, methyl ester To a mixture of 9 g of 2-methyl-2-thiopseudourea sulfate in 6 ml of water there is added 5.7 ml of methyl chloroformate at 0° C. and the mixture is stirred for 15 minutes. Then there is added 12 ml of 25% NaOH dropwise and the mixture is stirred for 15 minutes. Then there is added 6 ml of acetic acid dropwise and the mixture is stirred for 15 minutes. The total amount of 4-(cyclopropylmethyl)thio-o-phenylenediamine from above in 50 ml of methanol is then added and the mixture is refluxed for 2 hours. The alcohol is removed in vacuo and water is added. The resulting solid is filtered off and crystallized from glyme-acetonitrile to yield 3.9 g, m.p. 228°–231°.

D. [5-[(Cyclopropylmethyl)sulfinyl]-1H-benzimidazol-2-yl]carbamic acid, methyl ester To a solution of 2.77 g of [5-[(cyclopropylmentyl)thio]-1H-benzimidazol-2-yl]carbamic acid, methyl ester in 120 ml of chlororoform and 120 ml of acetic acid at −20°, there is added at once a solution of 2.1 g of m-chloroperbenzoic acid in 20 ml of chloroform. The stirred mixture is allowed to react slowly at room temperature after 4 hours of stirring. The chloroform is evaporated in vacuo. The remaining mixture is neutralized with aqueous sodium bicarbonate. The resulting solid is filtered off and crystallized from glyme to yield 1.2 g, m.p. 223°–224° of the title compound.

E. Feed Formulation of [5-[(Cyclopropylmethyl)sulfinyl]-1H-benzimidazol-2-yl]carbamic acid, methyl ester A feed formulation suitable for oral administration is prepared by dispersing 1.25 g of [5-[(cyclopropylmethyl)sulfinyl]-1H-benzimidazol-2-yl]carbamic acid, methyl ester in about 5 kg of mash feed. The resulting feed contains 0.025% by weight of the benzimidazole compound.

EXAMPLE 2

Testing of Feed Formulation Containing [5-[(Cyclopropylmethyl)sulfinyl]-1H-benzimidazol-2-yl]carbamic acid, methyl ester The following test is carried out to determine the effectiveness of treating turkeys to inhibit onset of histomonas (blackhead disease).

The feed formulation of Example 1 is given in the diet of 4 turkeys for 48 hours. Thereafter 8 turkeys (including the 4 turkeys treated with the Example 1 feed formulation) are inoculated with approximately 200 eggs of the nematode *Heterakis gallinarum* known to contain the protozoan *Histomonas meleagridis*. Four additional turkeys served as non-infected non-medicated controls.

After 21 days, the livers and ceca of all turkeys in the test and control groups are examined. The results obtained indicate that the turkeys which are fed the feed formulation of Example 1 appear normal when compared to a non-infected non-medicated group of turkeys. Fifty percent (50%) of the infected, non-medicated control turkeys died from blackhead disease and cheesy cecal cores and liver lesions (indicative of blackhead disease) are observed in the infected, non-medicated survivors.

The above data demonstrate that the feed formulation containing 0.025% by weight [5-[(cyclopropylmethyl)sulfinyl]-1H-benzimidazol-2-yl]carbamic acid, methyl ester is effective in inhibiting onset of blackhead disease in turkeys.

EXAMPLES 3 to 12

In a manner similar to that described in Examples 1 and 2, the following compounds are incorporated in feed formulations and are tested for their effectiveness in inhibiting onset of and/or combatting blackhead disease in turkeys:

3. [5-[(n-propyl)sulfinyl]-1H-benzimidazol-2-yl]-carbamic acid, methyl ester;

4. [5-[(2-methylpropyl)sulfinyl]-1H-benzimidazol-2-yl]carbamic acid, methyl ester;

5. [5-(benzylsulfinyl)-1H-benzimidazol-2-yl]carbamic acid, methyl ester;

6. [5-[(2,2-dichlorocyclopropylmethyl)sulfinyl]-1H-benzimidazol-2-yl]carbamic acid, methyl ester;

7. [5-[[(2,2-dichloro-1-methylcyclopropyl)methyl]sulfinyl]-1H-benzimidazol-2-yl]carbamic acid, methyl ester;

8. [5-[[(cyclohexen-2-yl)methyl]sulfinyl]-1H-benzimidazol-2-yl]carbamic acid, methyl ester;

9. [5-[[(3,4-dimethyl)cyclohexylmethyl]sulfinyl]-1H-benzimidazol-2-yl]carbamic acid, methyl ester;

10. [5-(cyclopropylsulfinyl)-1H-benzimidazol-2-yl]carbamic acid, methyl ester;

11. [5-[(cyclohexen-2-yl)sulfinyl]-1H-benzimidazol-2-yl]carbamic acid, methyl ester; and 12. [5-(phenylsulfinyl)-1H-benzimidazol-2-yl]carbamic acid, methyl ester.

Feed formulations as described in Example 1 containing the above benzimidazoles are found to inhibit onset of blackhead disease in turkeys inoculated with eggs of the nematode *Heterakis gallinarum* known to contain the protozoan *Histomonas meleagridis*.

What is claimed is:

1. A method of treating blackhead disease in birds, which comprises administering to a bird a therapeutically effective amount of a compound of the structure

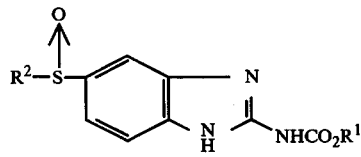

wherein $R^1$ is lower alkyl or phenyl-lower alkyl, and $R^2$ is lower alkyl, cycloalkyl, cycloalkylalkyl, cycloalkenyl, cycloalkenylalkyl, benzyl or phenylethyl, dispersed in a non-toxic physiologically acceptable carrier.

2. The method as defined in claim 1 wherein $R^2$ is cycloalkyl or cycloalkylalkyl.

3. The method as defined in claim 1 wherein $R^2$ is cycloalkylalkyl.

4. The method as defined in claim 1 wherein $R^2$ is cycloalkenyl.

5. The method as defined in claim 1 wherein $R^2$ is cycloalkenylalkyl.

6. The method as defined in claim 1 wherein $R^2$ is lower alkyl.

7. The method as defined as defined in claim 1 wherein $R^2$ is benzyl or phenethyl.

8. The method as defined in claim 1 wherein $R^2$ is isobutyl or 2,2-dichlorocyclopropylmethyl.

9. The method as defined in claim 1 wherein $R^1$ is lower alkyl or benzyl.

10. The method as defined in claim 1 wherein $R^2$ is cycloalkylalkyl and $R^1$ is lower alkyl.

11. The method as defined in claim 10 wherein $R^2$ is cyclopropylmethyl, cyclobutylmethyl or cyclohexylmethyl.

12. The method as defined in claim 11 wherein said compound has the name [5-[(cyclopropylmethyl)sulfinyl]-1H-benzimidazol-2-yl]carbamic acid, methyl ester.

13. The method as defined in claim 1 wherein $R^2$ is benzyl or phenylethyl.

14. The method as defined in claim 1 wherein said compound and carrier are administered parenterally.

15. The method as defined in claim 1 wherein said compound and carrier are administered orally.

* * * * *

UNITED STATES PATENT AND TRADEMARK OFFICE
CERTIFICATE OF CORRECTION

PATENT NO. : 4,127,664

DATED : November 28, 1978

INVENTOR(S) : Rudiger D. Haugwitz et al.

It is certified that error appears in the above-identified patent and that said Letters Patent are hereby corrected as shown below:

Column 1, line 18, "$R_2$" should read --$R^2$--.

Column 6, line 49, "Histomanas" should read --Histomonas--.

Signed and Sealed this

Twenty-seventh Day of March 1979

[SEAL]

Attest:

RUTH C. MASON
Attesting Officer

DONALD W. BANNER
Commissioner of Patents and Trademarks